United States Patent [19]
Lambert

[11] Patent Number: 6,155,255
[45] Date of Patent: Dec. 5, 2000

[54] VAPORIZER, USE OF SUCH VAPORIZER AND A METHOD FOR VAPORIZING A LIQUID

[75] Inventor: Hans Lambert, Stockholm, Sweden

[73] Assignee: Louis Gibeck AB, Upplands Väsby, Sweden

[21] Appl. No.: 09/147,079

[22] PCT Filed: Mar. 17, 1997

[86] PCT No.: PCT/SE97/00447

§ 371 Date: Oct. 1, 1998

§ 102(e) Date: Oct. 1, 1998

[87] PCT Pub. No.: WO97/36628

PCT Pub. Date: Oct. 9, 1997

[30] Foreign Application Priority Data

Apr. 1, 1996 [SE] Sweden .................................. 9601028

[51] Int. Cl.[7] .................................................. A61M 15/00
[52] U.S. Cl. .................... 128/203.16; 128/203.12
[58] Field of Search ................ 128/203.12, 203.16,
128/204.13, 203.24, 203.25, 202.22, 204.28,
205.11, 205.23; 261/99, DIG. 65

[56] References Cited

U.S. PATENT DOCUMENTS

| | | |
|---|---|---|
| 3,540,445 | 11/1970 | Moyat . |
| 4,015,599 | 4/1977 | Peterson . |
| 4,059,657 | 11/1977 | Hay .................................. 261/DIG. 65 |
| 4,454,879 | 6/1984 | Peterson . |
| 5,293,865 | 3/1994 | Altner et al. ........................ 128/203.12 |
| 5,337,738 | 8/1994 | Heinonen ............................ 128/203.12 |
| 5,490,500 | 2/1996 | Reichert et al. .................... 128/204.13 |
| 5,664,561 | 9/1997 | Kersey ................................ 128/203.26 |
| 5,730,119 | 3/1998 | Lekholm ............................ 128/203.12 |

FOREIGN PATENT DOCUMENTS

| | | |
|---|---|---|
| 41 05 163 A1 | 8/1992 | Germany . |
| 2255912 | 11/1992 | United Kingdom . |
| 2279015 | 12/1994 | United Kingdom . |

*Primary Examiner*—Aaron J. Lewis
*Assistant Examiner*—Teena Mitchell
*Attorney, Agent, or Firm*—Oblon, Spivak, McClelland, Maier & Neustadt, P.C.

[57] ABSTRACT

The invention relates to a vaporizing having a vaporizing chamber which includes a gas inlet and a gas outlet. The vaporizing chamber accommodates a porous liquid delivery device which communicates with an external liquid source via liquid supplier. Liquid to be vaporized is exposed to the by-passing gas through the medium of the liquid delivery device. According to the invention, the liquid is exposed to the gas exclusively via the pores in the liquid delivery device and the liquid supplier are controllable. The vaporizer is intended for use in the treatment of patients, preferably for administering an anaesthetic. The present invention also relates to a vaporizing method applied with the aid of the inventive vaporizer.

14 Claims, 6 Drawing Sheets

VAPORIZER, USE OF SUCH VAPORIZER AND A METHOD FOR VAPORIZING A LIQUID

FIELD OF INVENTION

According to a first aspect, the present invention relates to a vaporizer of the kind defined in the preamble of Claim 1. According to a second aspect, the invention relates to the particular use of such a vaporizer, and in accordance with a third aspect the invention relates to a liquid vaporizing method of the kind defined in the preamble of Claim 14.

Although the invention can be applied in several different ways, it finds particular use in the anaesthesia of patients, in which case the inventive vaporizer is adapted for connection to a system of hoses and apparatus that deliver breathing gas to a patient and that supply vaporized anaesthetic to respective patients.

DESCRIPTION OF THE BACKGROUND ART

Anaesthetic vaporizers are well known in the art and a large number of different methods of application are described in the literature. For a better understanding of the known and used vaporizers, reference is made to Anaesthetic Equipment, C. S. Ward, publisher Bailliere Tindall, 2nd edition, 1987, pp. 78–103, and to Anesthesia Vaporizers by J. B. Eisenkraft in Anesthesia Equipment, principles and applications, authors Jan Ehrenwerth, James B. Eisenkraft, publisher Mosby 1993, pp. 57–58.

The earlier described vaporizers are based on the principle of storing the liquid anaesthetic in a container. A breathing gas is introduced into this container and caused to pass over the surface of the liquid or to percolate therethrough.

Some of the anaesthetic is vaporized during passage of the breathing gas and therewith delivered to the patient together with the gas. This method, however, is encumbered with a large number of problems.

1. As the anaesthetic is vaporized, energy is removed from the gasified liquid, therewith cooling the gas. This cooling of the gas can result in a change in the vapor pressure across the liquid, and therewith in changes in the amount of anaesthetic that is entrained with the breathing gas.

In an endeavour to overcome this problem, additional heat is supplied in a number of constructions or, in the case of temperature-sensitive systems, the amount of breathing gas that passes across the liquid surface is varied and different gas flows are then combined so as to obtain a constant anaesthetic concentration in the breathing gas.

2. Vaporization of the anaesthetic is contingent on the rate of flow of the breathing gas. It has been endeavored to compensate for this dependency, by including different intricate flow-dependent valves and gas mixing systems in the vaporizer. This flow dependency can cause problems, particularly in the case of low fresh-gas inlet flows used in so-called low flow systems.

3. Different anaesthetics have different vaporization characteristics and must be applied in given concentrations for optimal anaesthesia. Attempts have been made to compensate for this, by designing individual vaporizers for solely one anaesthetic. One serious drawback in this regard is that erroneous filling of a given vaporizer with an anaesthetic for which the vaporizer is not intended can have catastrophic effects. The requirement of several different vaporizers mounted together on an anaesthesia machine also introduces the risk of all vaporizers being in operation simultaneously, with the danger of overdosing the anaesthetic.

4. Anesthetics have different vaporization characteristics in different gas mixtures. This can result in administering to the patient an anaesthetic concentration that is different to the concentration for which the vaporizer is set, due to the composition of the gas mixture.

5. A number of systems are based on the principle of submerging a wick in the anaesthetic. The anaesthetic is sucked up by the wick and vaporized on its surface. One drawback with this system, however, is that the suction rate is dependent on the height and temperature of the liquid surface, whereby the vaporizer must include a compensating system.

DE-A 4 105 163 teaches an anaesthetic vaporizing system in which a porous body is saturated with anaesthetic and through which the anaesthetizing gases pass.

One drawback with this system is that the total quantity of anaesthetic to be used is limited to the absorbency of the porous body. Another drawback is that evaporation of the anaesthetic in the by-passing gas will vary with time, due to lowering of the temperature of the body among other things (this lowering of temperature being caused by gas evaporation). The system must therefore include a separate temperature control circuit in order for the system to function satisfactorily. The system includes no pump or active supply means for delivering anaesthetic gas to the absorption-desorption material.

U.S. Pat. No. 4,0155,599 discloses that the absorbent maintains the anaesthetic in a two-dimensional state (it is not clear from the document what is meant by this). The anaesthetic is kept in a liquid state by means of a wick on the other hand. This system also includes a charged bed of absorbent through which gases pass. One drawback with this known system is that the temperature must be controlled and that different evaporation-absorption rates are obtained with mutually different anaesthetic gases.

U.S. Pat. No. 3,540,445 describes a vaporizer in which fibrous wicks are replaced with porous synthetic plastic materials that absorb the anaesthetic from a container through the medium of capillary forces. Although the container can be replenished, or topped-up, the amount of anaesthetic delivered to the by-passing breathing gas is determined mainly by evaporation from the porous plastic rods and the capillary forces within the rods (when the anaesthetic is maintained at a constant level in the container), wherewith the system becomes temperature-dependent and also contingent on the anaesthetic to be vaporized.

GB 2 255 912 describes a system that includes porous rods through which part of the gas passes while another part of the gas passes past the rods. The rods are supplied with gaseous anaesthetic, by submerging the rods in liquid anaesthetic. The system includes a level regulator which functions to control the level of the liquid anaesthetic in relation to the rods. It is necessary to control the rods and the temperature of the anaesthetic and the gas, in order to obtain a stable concentration of anaesthetic in the gas.

GB 2 279 015 describes a device in which the liquid to be vaporized is exposed to the breathing gas, partly through the medium of pores and partly through the medium of the free liquid surface. Consequently, the device also includes temperature control means. The device has no facility that enables liquid volumes to be regulated.

SUMMARY OF THE INVENTION

The object of the present invention is to eliminate several of the drawbacks of the aforedescribed systems and to provide a method and a device which will enable uniform vaporization of a large number of liquid anesthetics in a large number of different gas mixtures and gas flows to be achieved.

According to the invention, this object is achieved with a device of the kind defined in the preamble of Claim 1 and having the characteristic features set forth in the characterizing clause of said Claim, and also by virtue of a method of the kind defined in the preamble of Claim 14 and comprising the particular steps set forth in the characterizing clause of the method Claim.

Thus, the invention is based on actively supplying the liquid to be vaporized to the liquid delivery device, therewith eliminating the drawbacks associated with those types of systems in which the vaporizer is charged with an initial quantity of liquid that is consumed in the course of the process and thereby influences the vaporization process, for instance such as in systems of the kind exemplified in the first three of the aforementioned patent publications.

The invention is based on the same liquid delivery principle as that described in the aforementioned publication GB 2 255 912, where liquid is supplied constantly to the liquid delivery device from an external liquid source. However, the particular features of the present invention eliminate those problems that are created by the construction of this known arrangement of porous rods that are partially immersed in a liquid whose free surface is in contact with the by-passing breathing gas and in which arrangement the rods used in the process of vaporization are sensitive to variations in liquid level. Thus, the liquid is exposed in the liquid delivery device exclusively through its pores, therewith eliminating the influence of the free surface level. Because this exposure is effected exclusively through the medium of the pores, the amount of vaporized anaesthetic delivered is determined solely by the pump delivery rate. There is also obtained a large and constant exposure surface area, so that the rate of vaporization will be at least equal to the rate at which liquid is supplied and can also be regulated in a reliable and purposeful manner.

Because the liquid delivery devices can be regulated, the variation in requirement can be readily adapted, for instance in respect of different types of liquid to be vaporized.

In the case of one preferred embodiment of the invention, the liquid is supplied by means of a pump, preferably a motor-driven pump such as to achieve a positive and uniform supply and also to enable the supply to be readily adjusted.

In the case of another preferred embodiment, the concentration of vaporized liquid in the outgoing air is determined, preferably by an optical sensor conveniently adapted to control adjustment to the amount of liquid supplied.

A preferred use of the inventive apparatus relates to the treatment of human beings or animals, preferably human and animal anaesthesia.

These embodiments and other preferred embodiments of the invention are set forth in the dependent Claims.

The invention will now be described in more detail with reference to preferred embodiments thereof and also with reference to the accompanying drawings.

BRIEF DESCRIPTION OF THE DRAWINGS

FIGS. 6–8, 6a–8a illustrate various alternative embodiments in a manner corresponding to FIGS. 1, 1a.

DETAILED DESCRIPTION OF PREFERRED EMBODIMENTS

Figure 1:
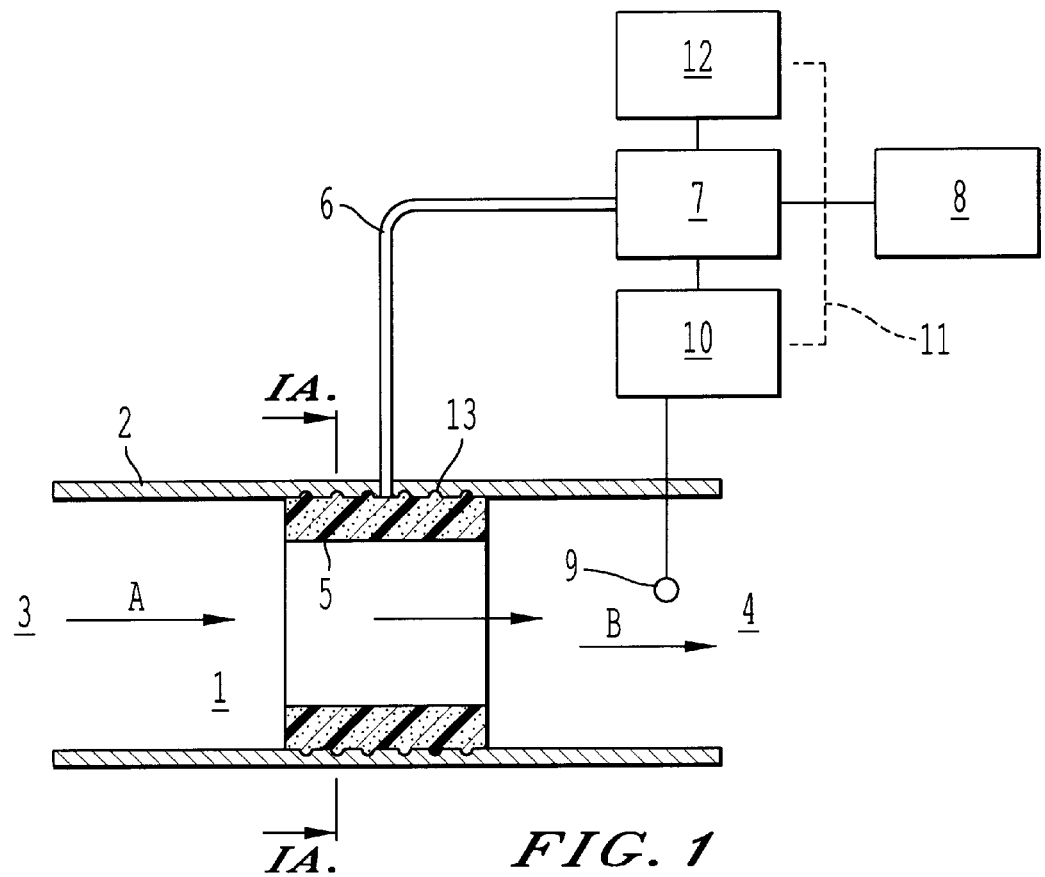
FIG. 1 illustrates the principle components of an arrangement according to a preferred embodiment.

Shown in FIG. 1 is a vaporization chamber 1 formed by a container 2. The illustrated container is tubular, although it may have any desired shape. The vaporization chamber 1 has an inlet opening 3 connected to a gas inlet line (not shown), as symbolized with the arrow A, and an outlet opening 4 connected to a gas outlet line (not shown), as symbolized with the arrow B. The gas outlet line is intended for connection to patient respiratory devices, in the illustrated case for the delivery of anaesthetic gas. A liquid delivering device 5 in the form of a porous body is disposed in the vaporization chamber 1. The porous body is cylindrical and is preferably made of a plastic material. A supply line 6 for supplying liquid anaesthetic is connected to the liquid delivery device 5.

Figure 1A:
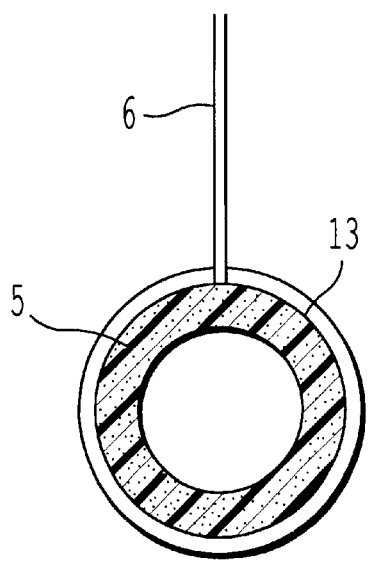
FIG. 1a is a sectional view taken on the line I—I in FIG. 1.

In FIG. 1a, the liquid delivery device is illustrated in cross section. In the inner wall of the container 2, there are provided grooves 13 arranged around the liquid delivery device 5 in order to efficiently distribute the liquid around the outer periphery of the complete porous body.

As the gas flows through the chamber 1 from the inlet 3 to the outlet 4, it passes the liquid delivery device 5 and comes into contact with the liquid present in the pores in said device. When the liquid is exposed to the by-passing gas, the liquid will evaporate to provide a vapor. Fresh liquid is constantly delivered from the supply line 6 through the passageways formed by the internal pores of the porous body and extending to the surface located pores, so that the process will, in principle, be continuous. The outflowing gas B will therewith contain a certain amount of vaporized anaesthetic.

The supply line 6 communicates with the annular grooves 13 which are formed around the outer circumferential surface of the liquid delivery device 5.

The liquid delivered from the supply line 6 is conducted directly to the pores of the liquid delivering device 5. This supply is thus active and is not achieved by connecting the liquid delivery device to any form of reservoir from which liquid is sucked into the pores by capillary action. This avoids control problems and also those problems of achieving a uniform flow that result from the use of such capillary supply. Because the liquid is delivered directly to the pores, the liquid will be exposed to the breathing gas exclusively through the medium of said pores and not through the medium of a free liquid surface.

In the illustrated embodiment, liquid anaesthetic is supplied with the aid of a pump which operates to supply the liquid delivery device 5 with anaesthetic taken from an external container 8.

Alternatively, the external container 8 may be positioned at a height sufficient to supply the liquid gravitationally. In this case, the pump 7 is replaced with a control valve.

A sensor 9 is placed in the gas stream, downstream of the liquid delivery device 5. The sensor may be an optical sensor that reads the optical absorption of the gas at different light wavelengths.

Alternatively, the sensor may have the form of an opening that is connected to a hose through which a gas sample is drawn off. The sensor 9 is connected to a signal unit 10 which sends signals to a pump control unit 12 via a signal line 11.

When an optical sensor is used, the signal unit 10 is comprised of a signal converter which forwards a relevant signal to the control unit 12 in response to the sensor reading. When the sensor 9 has the form of a sampler, the signal unit 10 is comprised of an analysis instrument which analyzes the contents of the sample and sends signals to the control unit 12 in response thereto.

The control unit 12 may be electric, electronic or electromechanical, although it will preferably be microprocessor controlled. The control unit influences the pump flow, either by varying the operating conditions of the motor or by varying the operating conditions of the pump directly. The control unit 12 and the pump 7 may conveniently be incorporated in a common unit. The pump may be an injection pump.

By means of the described control device, the amount of liquid anaesthetic delivered to the liquid delivery device 5 per unit of time is controlled by the amount of anaesthetic in the exiting gas B.

FIGS. 2 to 5 illustrate different ways of connecting the inventive vaporizer to an anaesthetic supply system through which gaseous anaesthetic is administered to a patient.

Figure 2:
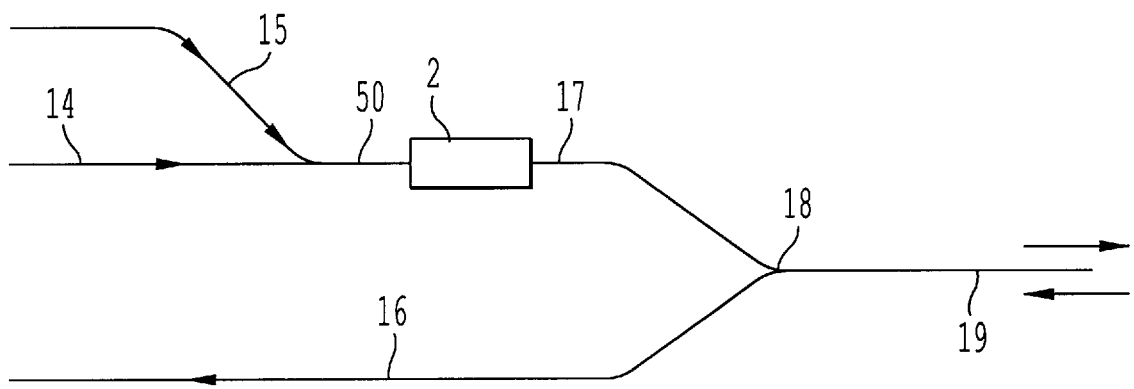
FIGS. 2–5 illustrate schematically different ways of connecting the inventive arrangement when used to induce anaesthesia.

In the FIG. 2 illustration, the gas that flows into the container 2 through the line 50 is a mixture that comprises fresh gas taken from a line 15 and gas recycled through a line 14. The anaesthetic containing gas is passed from the outlet side through the line 17 to a patient connection 19, via one leg of a Y-coupling 18. The other leg of the Y-coupling 18 is comprised of an expiration line 16.

Figure 3:
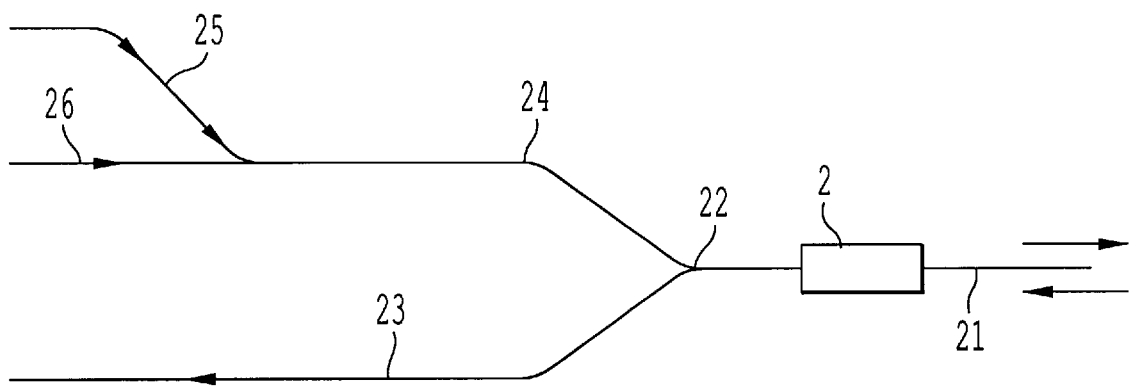

The coupling illustrated in FIG. 3 is a modified version in which the container 2 is connected between the Y-coupling 22 and the patient line 21. The reference numeral 24 identifies the inspiration hose, the numeral 25 identifies the fresh gas hose, and the numeral 26 identifies the hose for recycled gas, and numeral 23 identifies the expiration hose.

Figure 4:
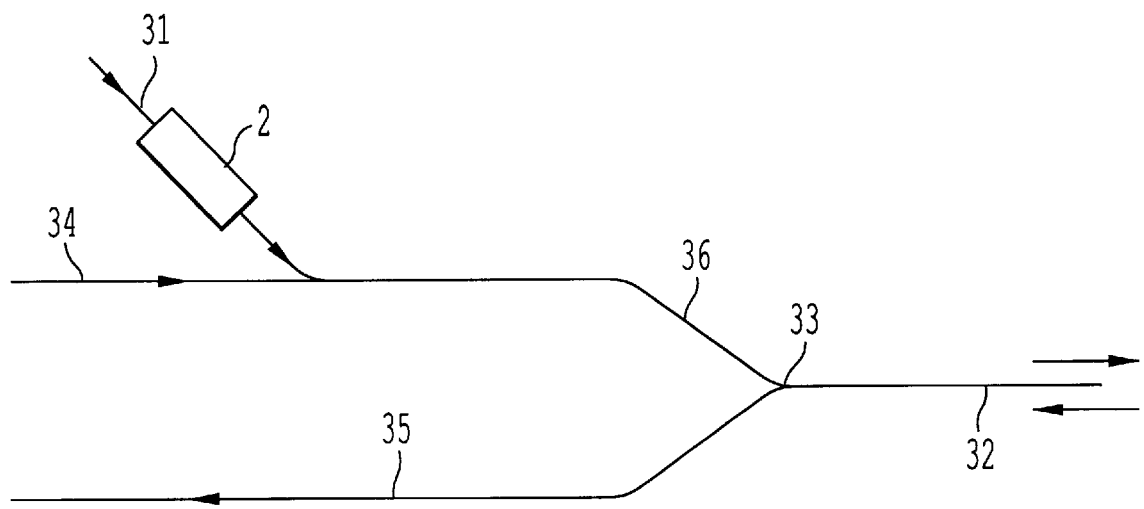

In the FIG. 4 embodiment, the container 2 is mounted in the fresh gas hose 31. In FIG. 4, the numeral 32 identifies the patient hose, reference numeral 33 identifies the Y-coupling, reference 34 identifies the recycled gas hose, 35 identifies the expiration hose, and 36 identifies the inspiration hose.

Figure 5:
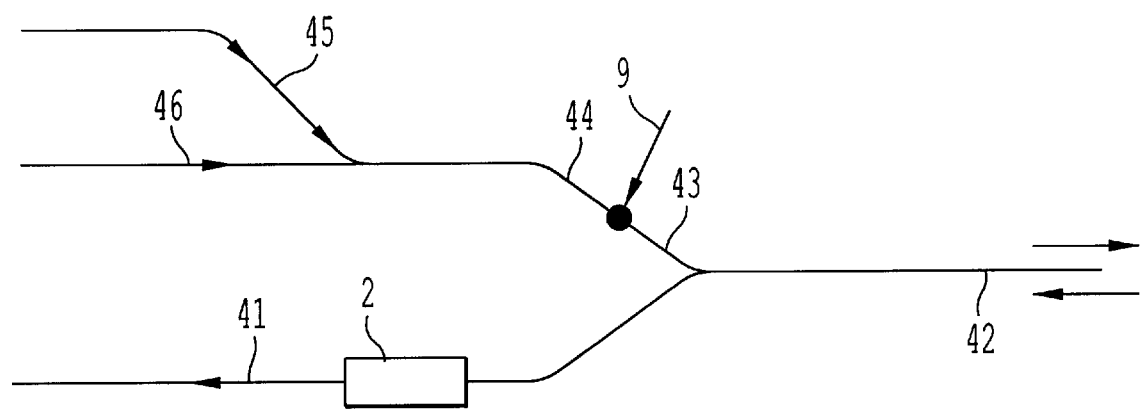

In the alternative shown in FIG. 5, the container 2 is mounted in the expiration hose 41. Reference 42 identifies the patient hose, 44 identifies the inspiration hose, 45 identifies the fresh air hose and 46 identifies the recycled gas hose. In this coupling arrangement, the sensor 9 is placed separate from the other components of the vaporizer arrangement, although in signal communication therewith, of course.

In the case of the FIG. 5 embodiment, the gas is enriched with anaesthetic in the expiration hose 41, so that the gas in the recycling hose 46 will contain gaseous anaesthetic. That part of the expiration hose 41 which is located downstream of the container 2, the recycling hose 46 and the inspiration hose 44 thus form parts of the container outlet line.

Figure 6:
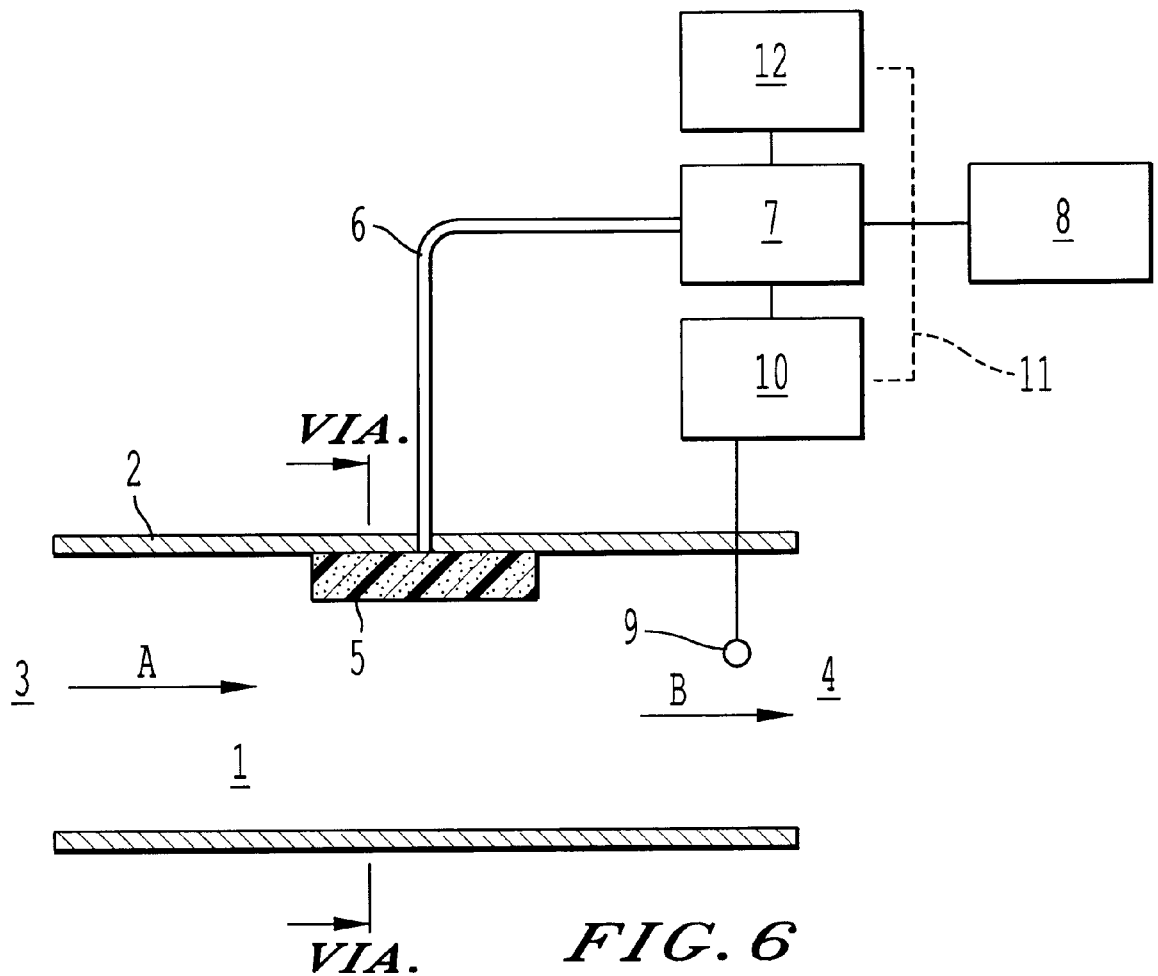
Figure 6A:
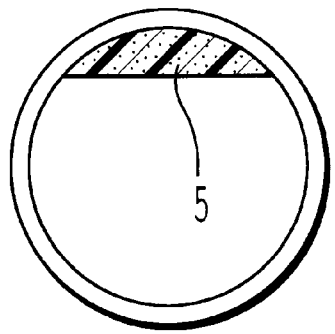
Figure 7:
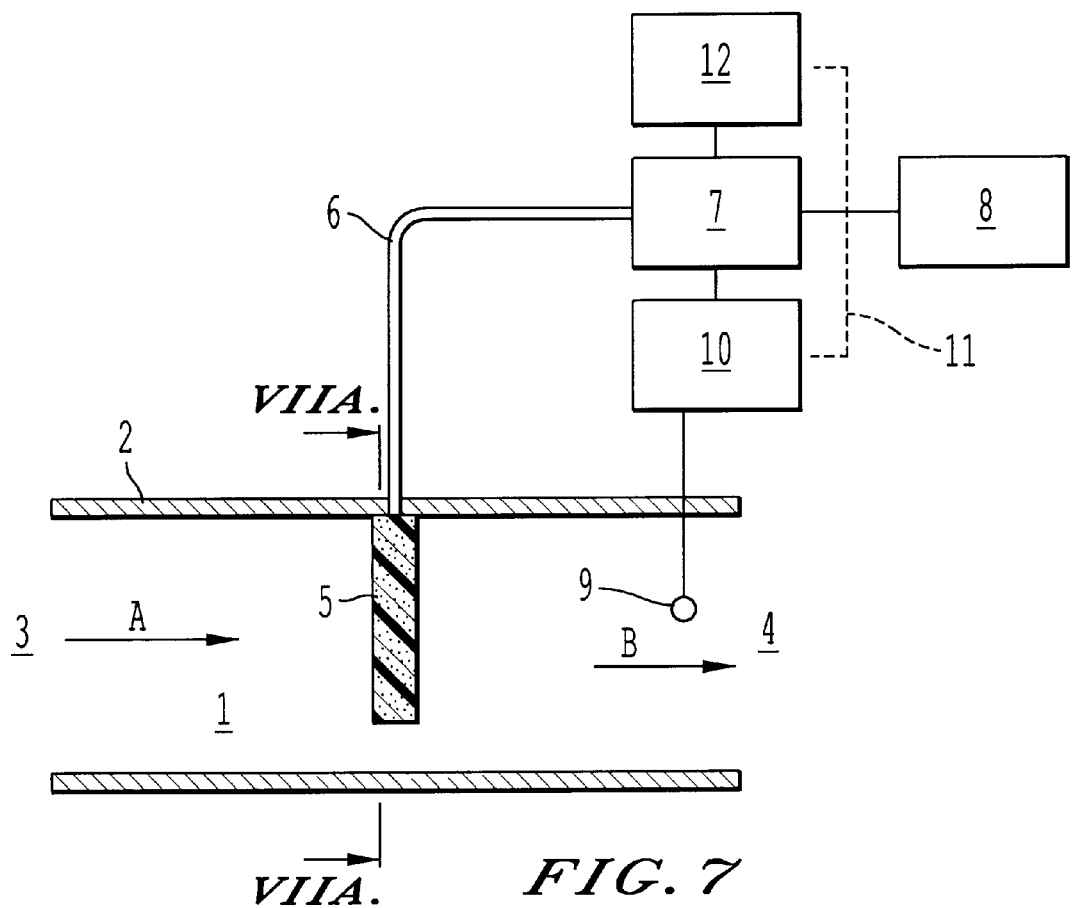
Figure 7A:
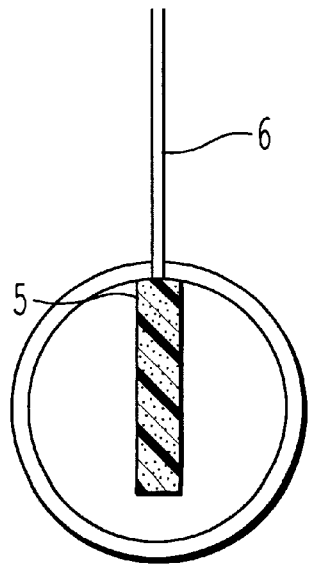
Figure 8:
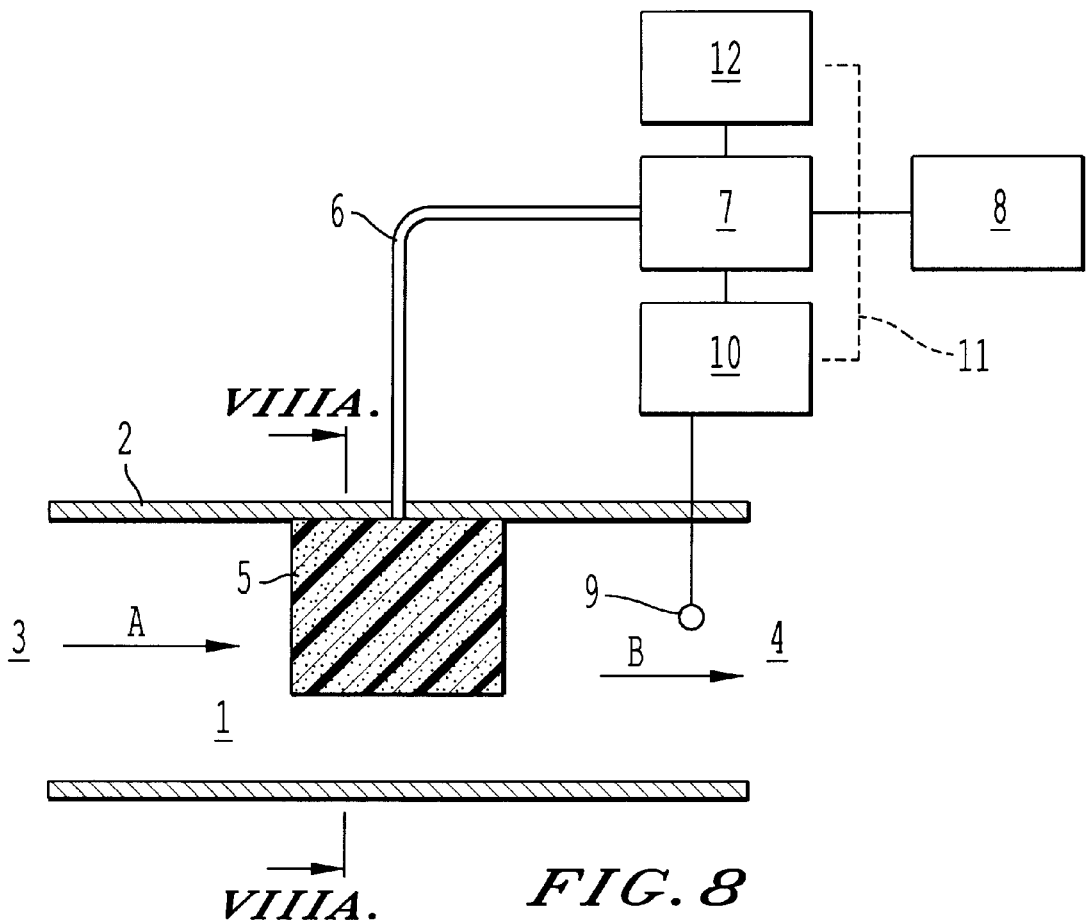
Figure 8A:
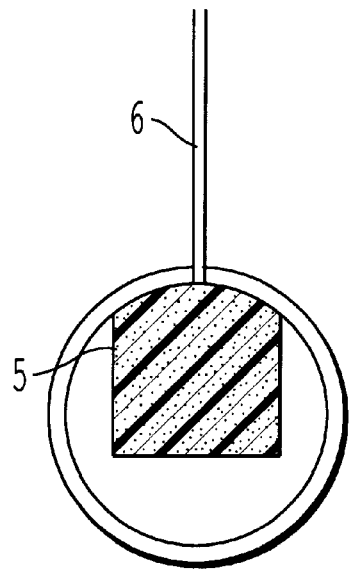

The devices shown in FIGS. 6–8 and 6a–8a are examples of modified embodiments of the liquid delivery device 5. In other respects they are substantially identical with the embodiment according to FIGS. 1 and 1*a*. In FIGS. 6 and 6*a*, the body 5 has the shape of a segment. In FIGS. 7 and 7*a*, the body 5 has a shape that is elongated perpendicular to the direction of the gas flow. In FIGS. 8 and 8*a*, the body 5 has a shape that is mainly rectangular, but having one side as a circular are corresponding to the inner surface of the container 2.

What is claimed is:

1. A vaporizer, comprising a vaporizing chamber which includes a gas inlet and a gas outlet and which accommodates a porous liquid delivery device adapted to expose a liquid to the vaporizing chamber for vaporization of said liquid, wherein said porous liquid delivery device is connected to a liquid supplier that communicates with an external liquid source, wherein said porous liquid delivery device is adapted to expose said liquid exclusively through pores in said porous liquid delivery device; and wherein said liquid supplier includes a liquid quantity regulator.

2. The vaporizer according to claim 1, wherein said gas outlet means includes a gas outlet line and an inspiration means connected thereto for the treatment of human beings or animals.

3. The vaporizer according to claim 2, wherein said liquid supplier means includes a pump.

4. The vaporizer according to claim 3, wherein said pump is controllable and therewith forms a component in said liquid quantity regulating means.

5. The vaporizer according to claim 3, wherein said pump is motor driven.

6. The vaporizer according to claim 5, wherein the liquid quantity regulator is adapted to deliver per unit of time a quantity of liquid that is at most equal to the quantity of liquid that is at most equal to the quantity of liquid that is vaporized per unit of time in said porous the liquid delivery device.

7. The vaporizer according to claim 5, comprising a sensor configured to sense the concentration of vaporized liquid, said sensor being provided downstream of said porous liquid delivery device.

8. The vaporizer according to claim 7, wherein the sensor includes an optical sensor.

9. The vaporizer according to claim 7, wherein said liquid quantity regulator is adapted to regulate the supply of liquid in response to said sensor.

10. The vaporizer according to claim 1, wherein said phorous liquid delivery device is made of plastic.

11. The vaporizer according to claim 1, wherein the liquid delivery device is in abutment with the inner surface of a vaporizing chamber wall; and in that the surface of the wall in abutment with the liquid delivery device includes a grooves which communicate with said liquid supplier.

12. A method of vaporizing a liquid, which comprises the steps of:

delivering a liquid from an external liquid source to a liquid delivery device; and exposing said liquid in said liquid delivery device to a flowing gas for vaporization of the liquid in contact with the gas, including, conducting said liquid to pores in said liquid delivery device exposing said liquid to the gas exclusively through said pores in said liquid delivery device, and regulating the supply of liquid delivered to said liquid delivery device.

13. The method according to claim 12, wherein the liquid is supplied with the aid of a motor driven pump.

14. The method according to claim 12, wherein the concentration of vaporized liquid in the gas is determined subsequent to contact of the gas with said liquid by means of an optical sensor, and wherein the amount of liquid supplied per unit of time is regulated in accordance with the sensed concentration.

* * * * *